United States Patent [19]

Klemm

[11] Patent Number: Plant 7,017

[45] Date of Patent: Sep. 5, 1989

[54] GERANIUM NAMED KLEDAPH

[75] Inventor: Siegfried Klemm, Stuttgart, Fed. Rep. of Germany

[73] Assignee: Klemm & Sohn, Stuttgart, Fed. Rep. of Germany

[21] Appl. No.: 244,313

[22] Filed: Sep. 15, 1988

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new and distinctive variety of geranium plant particularly distinguished by its profuse production of very large florets of a completely new crimson-pink coloration, about sixty of these florets together forming a very unusual cluster which is carried on an upright stem about 18 cm. in length extending from a strong stalk of about 8 to 9 cm. in length. This new geranium variety is further distinguished by its floriferous growth habit and its abundant production of light green foliage comprising medium sized, kidney-shaped leaves and standing about eight to ten inches above the soil, the total height of the plant being about 28 cm.

1 Drawing Sheet

BACKGROUND OF THE NEW PLANT

This new geranium cultivar originated as a seedling of a hybrid product by my crossing the variety 'PAC Isabell' (unpatented) with the pollen of the variety 'PAC 532' (unpatented), both selected from my geranium collection maintained for breeding purposes at my nursery at Stuttgart, West Germany. This new plant bloomed for the first time in 1986 and was propagated by me and under my direction, by means of cuttings, with very satisfactory results, wherefore propagation was continued through several successive generations by cuttings, whereby it was determined that the novel and distinctive characteristics of this new plant would hold true from generation to generation and appeared to be firmly fixed.

DESCRIPTION OF THE DRAWING

My new geranium cultivar is illustrated by the accompanying photographic drawing, which shows a fully developed potted plant with flowers in several stages of blooming, as well as bud clusters in several stages of development and the nature of the foliage, the color shown being as nearly true to that herein specified as is reasonably possible to obtain by conventional photographic procedures.

DESCRIPTION OF THE NEW PLANT

The following is a detailed description of my new geranium variety as observed of plants grown both in greenhouse and outdoors at Stuttgart with the color designation according to The R.H.S. Colour Chart published by The Royal Horticultural Society of London, England.

THE PLANT

Origin: Seedling.
Parentage:
- *Seed parent.*—'PAC Isabell' (unpatented).
- *Pollen parent.*—'PAC 532' (unpatented).

Classification:
- *Botanic.*—*Pelargonium zonale* Hybrid.
- *Commercial.*—Geranium.

Form: Very bushy.
Height: About 25 to 30 cm. above the soil.

Growth: Vigorous, upright, with good strength and at a medium growth rate.
Branching character: Normal.
Foliage:
- *Quantity.*—Moderately abundant.
- *Leaf size.*—Medium; about 7 cm. long and 5 cm. wide.
- *Leaf shape.*—Kidney-shaped with crenate margin.
- *Texture.*—Smooth.
- *Ribs and veins.*—6 to 7 veins of each leaf.
- *Color.*—Upper side — Medium Green, with slight zonation. Under side — Light Green, with slight showing of veins.

THE BUD

Size: Normal.
- *Diameter.*—About 9 to 10 mm.
- *Length.*—About 15 mm.

Shape: Ovoid to globular with pointed apex.
Rate of opening: Rapid.
Color of florets:
- *When sepals first divide.*—Pink.
- *When petals begin to unfurl.*—Carmesin Pink.

Sepals:
- *Number.*—Five.
- *Shape.*—Linear.
- *Character.*—The sepals stand up when the flowers open.
- *Color.*—Green.

Flower stem:
- *Length.*—About 18 cm.
- *Character.*—Upright and rigid.
- *Color.*—Green.

THE INFLORESCENCE

Blooming habit: Continuous and profusely from early Spring to late Fall.
Cluster size: Large.
Number of florets: About sixty in umbel formation.
Florets:
- *Size.*—Very large. Diameter — About 4.5 cm. Depth — About 1 cm.
- *Borne.*—Singly on the umbel stem of a cluster.
- *Shape.*—When bloom first opens, cup-shaped. When bloom matures, flat cup.

Petalage:

*Number of petals.*—Seven to nine.

*Arrangement.*—Imbricated.

*Form.*—Wide ovate with entire margin and round apex.

*Texture.*—Soft.

*Appearance.*—Satiny.

*Color.*—R.H.S. 52-A.

Petaloids:

*Number.*—Two or three.

*Size.*—About 4 or 5 mm.

*Color.*—Carmesin Pink.

Effect of weather: Very slight.

Discoloration after full bloom: Very little.

Persistence: Very good.

Lasting quality: The petals stay on the florets for about fourteen days.

THE REPRODUCTIVE ORGANS

Stamens:

*Number.*—Seven.

*Arrangement.*—Around the ovary.

*Anthers.*—Size: About 1.5 cm. Color: Light Orange.

*Filaments.*—Length: About 3 to 4 mm. Color: White.

*Pollen.*—Color: Orange.

Pistil:

*Number.*—One.

*Style.*—Length: About 4 mm. Color: Light Pink and Green.

*Stigmas.*—Five cells. Color: Frosted Pink glas.

Character of Ovaries: Normal.

THE FRUIT

Fertility: The fruit is fertile.

Shape: Ovoid.

Color at Maturity: Brown.

It appears that this plant is of a new color in the *Pelargonium zonale* group, these plants are very floriferous and have ideal growing characteristics.

I claim:

1. The new variety of geranium plant, and the parts thereof, substantially as herein shown and described, particularly distinguished by its crimson-pink coloration, its very large, uniformly shaped florets, and its profuse production of blooms.

* * * * *

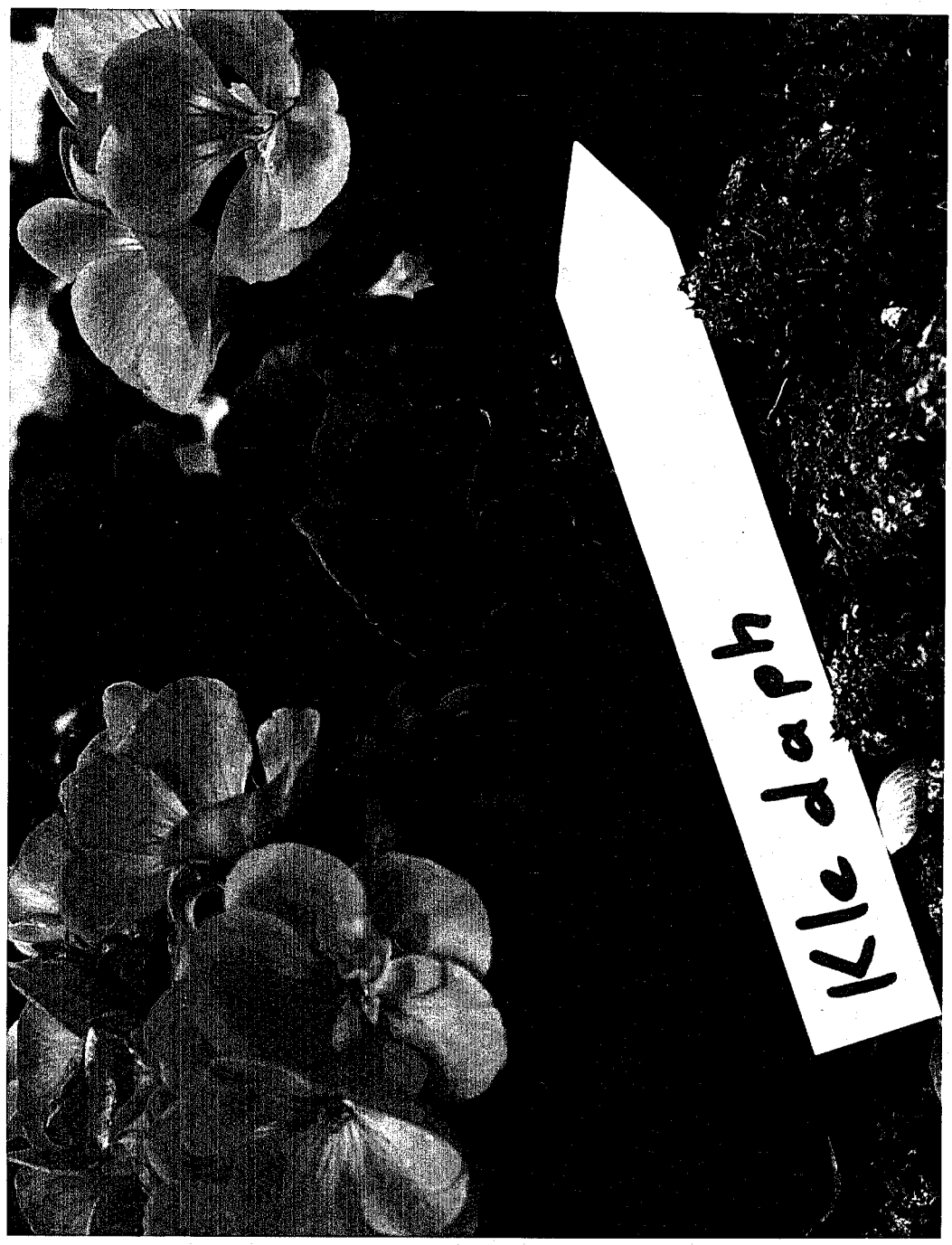
Kledaph